United States Patent [19]

Varma

[11] 4,213,912

[45] Jul. 22, 1980

[54] PROCESS FOR PREPARING STEROIDAL [16α,17-D]CYCLOHEXENE-21-CARBOXYLIC ACID ESTERS

[75] Inventor: Ravi K. Varma, Belle Mead, N.J.

[73] Assignee: E. R. Squibb & Sons, Inc., Princeton, N.J.

[21] Appl. No.: 33,351

[22] Filed: Apr. 26, 1979

[51] Int. Cl.$^2$ ................................................ C07J 5/00
[52] U.S. Cl. .............................. 260/397.1; 260/397.45
[58] Field of Search ....................................... 260/397.1

[56] References Cited

U.S. PATENT DOCUMENTS

| | | | |
|---|---|---|---|
| 3,937,720 | 2/1976 | Varma et al. | 260/397.1 |
| 3,944,584 | 3/1976 | Chao et al. | 260/397.45 |

*Primary Examiner*—Elbert L. Roberts
*Attorney, Agent, or Firm*—Lawrence S. Levinson; Donald J. Barrack

[57] ABSTRACT

Steroidal [16α, 17-d]cyclohexene-21-carboxylic acid esters can be prepared from 21-hydroxy-$\Delta^{16}$-steroids by first converting the starting steroid to a 21-carboxylic acid ester -$\Delta^{16}$-steroid and then fusing the cyclohexene ring to the 16,17-positions of the intermediate.

1 Claim, No Drawings

PROCESS FOR PREPARING STEROIDAL [16α,17-D]CYCLOHEXENE-21-CARBOXYLIC ACID ESTERS

RELATED APPLICATIONS

Copending U.S. Pat. application Ser. No. 919,006, filed June 26, 1978, now U.S. Pat. No. 4,160,772, issued July 10, 1979, discloses inter alia, steroid products having the formula

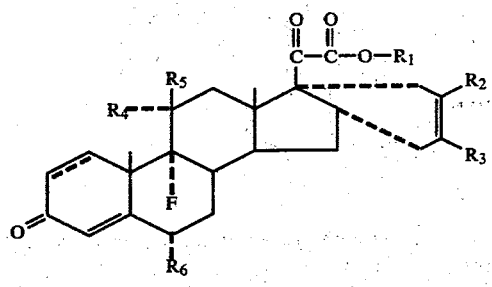

and steroid intermediates having the formulas

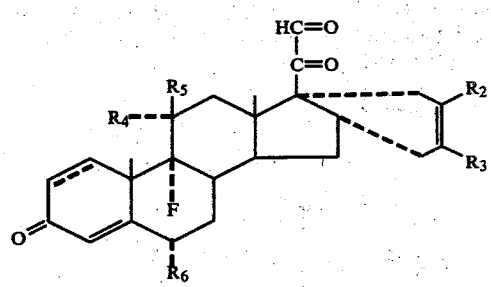

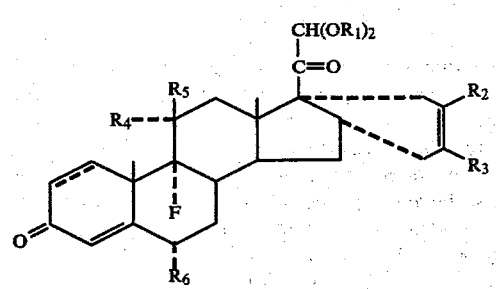

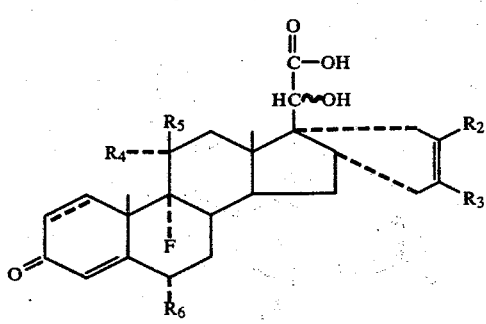

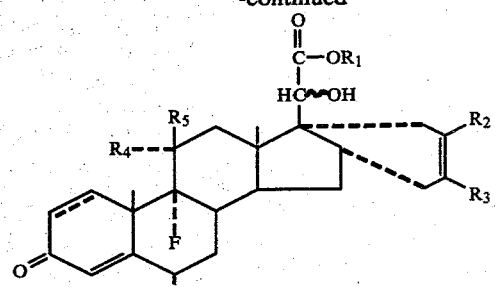

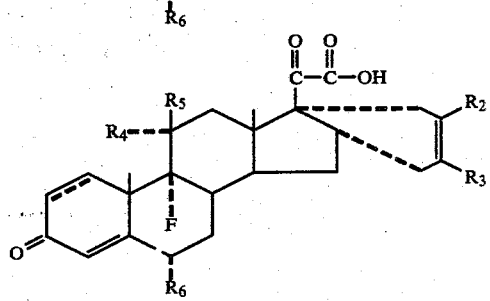

In the above formulas, the symbols are as defined hereinafter. The application teaches the preparation of the above steroid products utilizing as a starting material the corresponding 21-hydroxysteroidal[16α,17-d]cyclohexenes. The starting steroid can be oxidized in an alcohol ($R_1$-OH) solvent to a mixture of the corresponding aldehyde (formula II) and acetal (formula III) or to the corresponding 20-hydroxy-21-carboxylic acid ester (formula V) or acid (formula IV). Reacting a mixture of steroids of formulas II and III with an inorganic cyanide catalyst, an oxidizing agent, an inert solvent, an alcohol and an organic acid yields the product of formula I.

Copending U.S. Pat. application Ser. No. 33,357, filed Apr. 26, 1979, discloses a process for preparing steroidal [16α,17-b]naphthaleno-21-carboxylic acid esters utilizing intermediates disclosed herein.

BACKGROUND OF THE INVENTION

Antiinflammatory activity, topical and systemic, is exhibited by many steroids of the pregnene series. More specifically, steroidal [16α,17-d] cyclohexenes having the formula

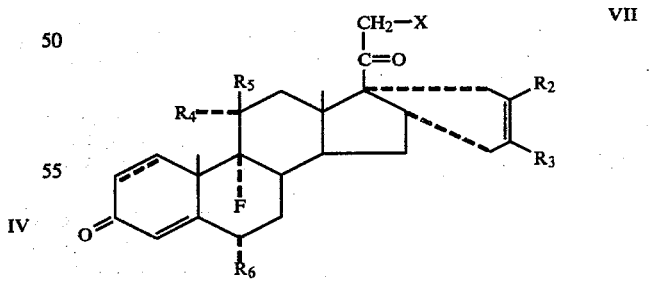

wherein X is hydrogen, hydroxy, halogen or acyloxy, and the "R groups" are as defined hereinafter, are disclosed as having topical and systemic antiinflammatory activity; see, for example, U.S. Pat. No. 3,944,584, issued Mar. 16, 1976.

The prior art also discloses various pregnene-21-oic acids and corresponding esters as having topical antiinflammatory activity, while being essentially inactive systemically. Exemplary disclosures are U.S. Pat. No. 3,919,421, issued Nov. 11, 1975; U.S. Pat. No. 3,956,347, issued May 11, 1976; U.S. Pat. No. 4,049,804, issued Sept. 30, 1977; and Laurent et al., *Journal of Steroid Biochemistry*, 6:185–192 (1975). One such pregnane derivative, fluocortin butyl ester (6α-fluoro-11β-hydroxy-16α-methyl-3,20-dioxopregna-1,4-diene-21-oic acid, butyl ester) has drawn particular attention and interest. Monder et al., *Journal of Steroid Biochemistry*, 8:897–908 (1977), discuss the synthesis of carboxylic acid derivates of steroids, and the existence of these derivatives as metabolites of steroids.

BRIEF DESCRIPTION OF THE INVENTION

Steroids having the formula

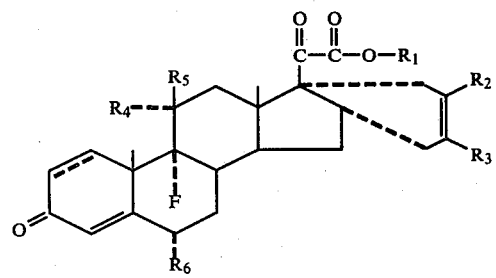

can be prepared from the corresponding 21-hydroxy-Δ¹⁶-steroid having the formula

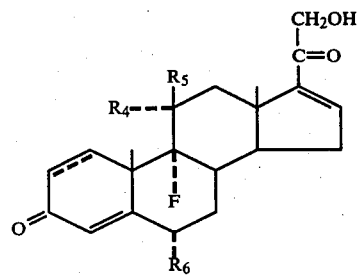

by first converting the 21-hydroxy group to a 21-carboxylic acid ester group and then fusing the cyclohexene group in the 16,17-position. In formulas I and VIII, and throughout the specification, the symbols are as defined below.

$R_1$ is alkyl of 1 to 10 carbon atoms, aryl, or arylalkyl;

$R_2$ and $R_3$ are the same or different and are hydrogen, alkyl or aryl;

$R_4$ is hydrogen and $R_5$ is hydroxy or together $R_4$ and $R_5$ are =O; and $R_6$ is hydrogen, methyl or fluorine.

The dotted lines in the 1,2-position of the steroids represent the optional presence of ethylenic unsaturation.

The term "aryl", as used throughout the specification, refers to phenyl or phenyl substituted with one or more halogen, alkyl and alkoxy groups.

The terms "alkyl" and "alkoxy", as used throughout the specification (unless otherwise defined), refer to both branched and straight chain groups having 1 to 8 carbon atoms. Groups having 1 to 4 carbon atoms are preferred.

The term "halogen", as used throughout the specification refers to fluorine, chlorine, bromine and iodine.

DETAILED DESCRIPTION OF THE INVENTION

The 21-hydroxy-Δ¹⁶-steroids of formula VIII, which form the starting point for the process of this invention, or the corresponding 21-acyloxy steroids are known in the art. The 21-acyloxy steroids are readily converted to the corresponding 21-hydroxy steroids using conventional techniques.

A steroid of formula VIII can be oxidized to the corresponding aldehyde having the formula

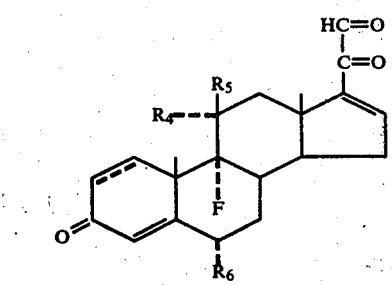

using a catalyst such as copper acetate. The reaction can be run in an alcohol solvent.

If the above described oxidation reaction is carried out in the presence of oxygen (e.g., by bubbling air through the reaction mixture), the reaction will generally yield, in addition to a steroidal-21-aldehyde of formula IX, the corresponding steroidal-21-acetal formed with the alcohol solvent ($R_1$—OH); i.e., a steroid having the formula

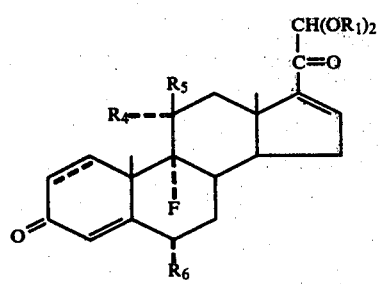

The oxidation reaction will generally be completed within a relatively short period of time, i.e., about 1 hour.

If the above-described reaction is allowed to proceed for an extended period of time, e.g., more than about 24 hours, the major product will be the 20-hydroxy-21-carboxylic acid ester having the formula

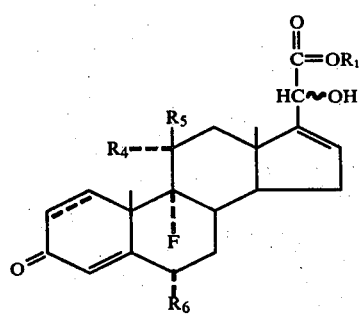

If water is present as a co-solvent in the oxidation reaction, and the reaction is allowed to proceed for an extended period of time, in addition to the 20-hydroxy-21-carboxylic acid ester of formula XI, the corresponding 20-hydroxy-21-carboxylic acid will be produced; i.e., a steroid having the formula

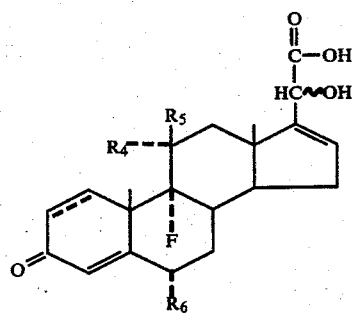

The steroids of formulas XI and XII exist as mixtures of the 20α- and 20β-hydroxy-steroids.

Reaction of a mixture of a steroidal-21-aldehyde of formula IX and the corresponding steroidal-21-acetal of formula X with a mixture of (i) an inorganic cyanide catalyst (e.g., an alkali metal cyanide such as potassium cyanide); (ii) an oxidizing agent, e.g., a heavy metal oxide such as activated manganese dioxide or lead dioxide; (iii) an inert solvent, e.g., a halogentated hydrocarbon solvent such as dichloromethane or chloroform; (iv) a primary or secondary alcohol, $R_1'$—OH (throughout the specification $R_1'$ is any nontertiary $R_1$ group); and (v) an acid, e.g., acetic acid, which serves to neutralize the alkali cyanide catalyst; yields a steroid having the formula

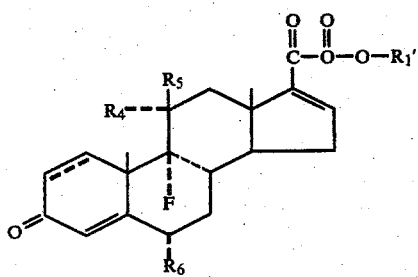

The 20α- and 20β-hydroxysteroids of formulas XI and XII can be oxidized to obtain the corresponding 20-ketosteroids, having the respective formulas

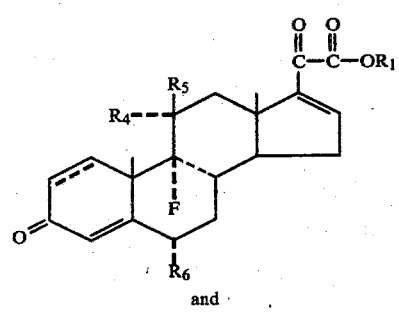

and

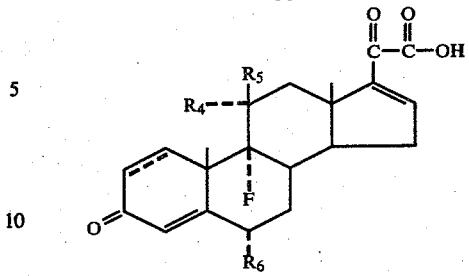

Exemplary of suitable oxidizing agents are manganese dioxide and chromium dioxide. In the instance wherein the 20α- and 20β-hydroxysteroids being oxidized have an 11β-hydroxy substituent, the steroids of formulas XIV and XV will be mixtures of 11β-hydroxy and 11-keto steroids.

The intermediates of formula XIV can also be prepared by esterification of the corresponding steroidal-21-oic acid of formula XV. (A steroid of formula XV can be prepared as described above, or alternatively, by saponification of a corresponding steroidal-21-oic acid ester of formula XIV.)

Still another route for the preparation of the intermediates of formula XIV wherein $R_1$ is a non-tertiary group is the transesterification of another ester of formula XIV. The starting steroid is reacted with the appropriate alcohol in the presence of a basic alkoxide (e.g., sodium ethoxide or aluminum isopropoxide) or, preferably, a source of cyanide ion (e.g., an alkali metal cyanide such as sodium cyanide or potassium cyanide) to yield the transesterification product.

A steroid of formula XIII or XIV can be converted to the corresponding product of formula I by reacting it with a butadiene having the formula

A steroid of formula XIII or XIV and a butadiene of formula XVI can be reacted to form a steroid of formula I using the Diels-Alder reaction. The preferred catalysts for the reaction are anhydrous aluminum chloride and anhydrous aluminum bromide. The reaction can be run in an organic solvent, e.g., a halogenated hydrocarbon such as dichloromethane. The above described Diels-Alder reaction is highly selective and takes place exclusively at the double bond in the 16-position, even in the presence of the $\Delta^{1,4}$-3-keto function. In those instances wherein the butadiene is unstable in the presence of a Lewis acid catalyst, the Diels-Alder reaction is run in the presence of a free radical inhibitor at elevated temperatures.

If the steroid of formula XIII or XIV contains an 11β-hydroxy group, it is desirable to first protect the group before running the Diels-Alder reaction. While many means of protecting the 11-functional group will be apparent to a person skilled in the steroid art, one particularly desirable method is the acylation of the group. The acylation reaction can be run using an acid anhydride, e.g., acetic anhydride in the presence of a Lewis catalyst, e.g., boron trifluoride etherate. After the Diels-Alder reaction has been run, the protective group can be removed using a conventional technique.

The following examples are specific embodiments of this invention.

EXAMPLE 1

9-Fluoro-11β-hydroxy-1', 2'-dimethyl-3,20-dioxopregna-1,4-dieno[16α, 17-d]cyclohexene-21-oic acid, n-butyl ester (A) 9-Fluoro-11β-hydroxy-3,20-dioxopregna-1,4,16-triene-21-carboxaldehyde and 9-fluoro-11β-hydroxy-21-dimethoxypregna-1,4,16-triene-3,20-dione A solution of 9-fluoro-11β,21-dihydroxypregna-1,4,16-triene-3,20-dione (1.7 g) is dissolved in methanol (300 ml) by warming and the solution is cooled to room temperature. Copper acetate (100 mg) is added and a stream of air is passed into the solution under stirring. In about 20 minutes the starting material disappears to give less polar compounds as indicated by thin layer chromatography. The solution is then evaporated in vacuo, the residual solid is washed successively with a dilute ammonium chloride solution and water and is dried to afford an essentially equimolar mixture (1.9 g) of the title aldehyde (as its hydrate) and the title acetal as indicated by the NMR spectrum. When dried in vacuo (125°–130° C., 0.5 mm of Hg) for 2.0 hours, this material is converted into an essentially equimolar mixture (1.77 g) of the title aldehyde and acetal as shown by NMR and IR spectra.

(B) 9-Fluoro-11β-hydroxy-3,20-dioxopregna-1,4,16-trieno-21-oic acid, methyl ester To a stirred solution of the mixture of aldehyde and acetal prepared in part A, in a mixture of anhydrous dichloromethane (100 ml) and anhydrous methanol (20 ml) is added successively activated manganese dioxide (4.0 g), potassium cyanide (500 mg) and glacial acetic acid (0.5 ml). In less than 1.0 hour, the starting materials disappear to give essentially a single less polar compound as indicated by thin layer chromatography. The reaction mixture is filtered through a bed of diatomaceous earth and the filter cake is washed with several small portions of a warm mixture of dichloromethane-methanol. The filtrate and the washings are combined and evaporated to a solid residue which is washed with water and dried. Crystallization of the resulting material from methanol-dichloromethane (with evaporative removal of dichloromethane) yields 1.4 g of the title compound, melting point 284°–286° C.

(C) 11β-(Acetyloxy)-9-fluoro-3,20-dioxopregna-1,4,16-trieno-21-oic acid, methyl ester A solution of 9-fluoro-11β-hydroxy-3,20-dioxopregna-1,4,16-trieno-21-oic acid, methyl ester (400 mg) in a mixture of glacial acetic acid (9.0 ml) and acetic anhydride (9.0 ml) containing p-toluenesulfonic acid (200 mg) is stirred at room temperature for 24 hours. Sodium acetate (300 mg) is added and the mixture is poured into ice water (200 ml) with stirring. The solid that separates is isolated by filtration, washed with water and dried to yield 400 mg of the title compound that is contaminated with only trace amount impurities as judged by thin layer chromatography. Crystallization of this material from ethyl acetate-hexane yields 350 mg of the title compound, melting point 235°–236° C.

(D) 11β-(Acetyloxyl)-9-fluoro-1', 2'-dimethyl-3,20-dioxopregna-1,4-dieno-[16α, 17-d]cyclohexen-21-oic acid, methyl ester To a stirred solution of 11β-(acetyloxy)-9-fluoro-3,20-dioxopregna-1,4,16-trieno-21-oic acid, methyl ester (320 mg) in anhydrous dichloromethane (25 ml) containing aluminum chloride (100 mg) is added 2,3-dimethyl-1,3-butadiene (0.25 ml). The mixture is stirred at room temperature for 1.5 hour, poured into water and extracted with dichloromethane. The dichloromethane extract is washed with water, dried over anhydrous magnesium sulfate and evaporated to a residue (300 mg). This is subjected to chromatography on a column of silica gel (10 g) to isolate the title compound (265 mg). Crystallization from ethyl acetate-hexane gives needles (160 mg), melting point 172°–173° C.

(E) 9-Fluoro-11β-hydroxy-1',2'-dimethyl-3,20-dioxopregna-1,4-dieno[16α,17-d]cyclohexen-21-oic acid.

A solution of 11β-(acetyloxy)-9-fluoro-1',2'-dimethyl-3,20-dioxopregna-1,4-dieno[16α,17-d]cyclohexen-21-oic acid, methyl ester (235 mg) in a mixture of 90% methanol (100 ml) and tetrahydrofuran (10 ml) containing 3 M sodium hydroxide (2.0 ml) is stirred under an atmosphere of nitrogen in a bath at 60°–70° C. for 2–3 hours. The mixture is acidified with the minimum amount of 5% hydrochloric acid and evaporated in vacuo. The residue is worked up with water and dried to yield 195 mg of the title compound. Crystallization from a mixture of chloroform-methanol gives the analytical specimen of the title compound, melting point 236°–239° C.

(F) 9-Fluoro-11β-hydroxy-1',2'-dimethyl-3,20-dioxopregna-1,4-dieno[16α,17-d]cyclohexen-21-oic acid, n-butyl ester.

To a solution of 9-fluoro-11β-hydroxy-1',2'-dimethyl-3,20-dioxopregna-1,4-dieno[16α,17-d]cyclohexen-21-oic acid (175 mg) in dichloromethane (40 ml) containing a few drops of methanol is added an excess of an ethereal solution of diazobutane. After 5 minutes, the excess diaxobutane is destroyed by the addition of a few drops of acetic acid. The solution is evaporated to dryness and the residue is crystallized from acetone-hexane to yield 127 mg of the title compound point 209°–211° C.

What is claimed is:
1. A process for converting a steroid having the formula

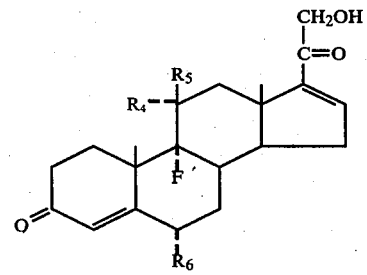

or the 1,2-dehydro derivative thereof, to a steroid having the formula

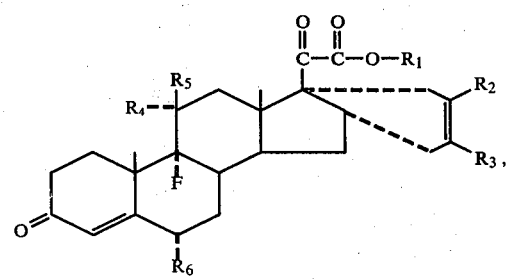

or the 1,2-dehydro derivative thereof, which comprises first converting the 21-hydroxy group of the starting steroid to a 21-carboxylic acid ester group and reacting the latter with a butadiene having the formula

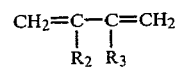

under Diels-Alder wherein
$R_1$ is alkyl of 1 to 10 carbon atoms, aryl, or arylalkyl;
$R_2$ and $R_3$ are the same or different and are hydrogen, alkyl or aryl;
$R_4$ is hydrogen and $R_5$ is hydroxy or together $R_4$ and $R_5$ are $=O$; and
$R_6$ is hydrogen, methyl or fluorine.

* * * * *

UNITED STATES PATENT OFFICE
CERTIFICATE OF CORRECTION

Patent No. 4,213,912          Dated July 22, 1980

Inventor(s) Ravi K. Varma

It is certified that error appears in the above-identified patent and that said Letters Patent are hereby corrected as shown below:

Column 10, line 6, after "Diels-Alder" should read:
--reaction conditions to obtain the C-16,17 cyclohexene derivatives wherein $R_1$ is alkyl of 1 to 10 carbon atoms, aryl, or arylalkyl;

$R_2$ and $R_3$ are the same or different and are hydrogen, alkyl or aryl;

$R_4$ is hydrogen and $R_5$ is hydroxy or together $R_4$ and $R_5$ are =O; and $R_6$ is hydrogen, methyl or fluorine.--

Signed and Sealed this

Eleventh Day of November 1980

[SEAL]

Attest:

SIDNEY A. DIAMOND

Attesting Officer          Commissioner of Patents and Trademarks